(12) United States Patent
Joanicot et al.

(10) Patent No.: US 8,420,397 B2
(45) Date of Patent: Apr. 16, 2013

(54) FLUID FLOW DEVICE AND ASSEMBLY EMPLOYING A TEMPERATURE GADIENT FOR DETERMINING AT LEAST ONE CHARACTERISTIC OF A PHYSICO-CHEMICAL SYSTEM THEREWITH

(75) Inventors: Mathieu Joanicot, Chatenay-Malabry (FR); Philippe Laval, Bordeaux (FR); Jean-Baptiste Salmon, Bordeaux (FR)

(73) Assignees: Rhodia Operations, Aubervilliers (FR); Centre National de la Recherche Scientifique (C.N.R.S.), Paris (FR)

( * ) Notice: Subject to any disclaimer, the term of this patent is extended or adjusted under 35 U.S.C. 154(b) by 244 days.

(21) Appl. No.: 12/445,213

(22) PCT Filed: Oct. 12, 2007

(86) PCT No.: PCT/FR2007/001667
§ 371 (c)(1),
(2), (4) Date: Sep. 2, 2010

(87) PCT Pub. No.: WO2008/046989
PCT Pub. Date: Apr. 24, 2008

(65) Prior Publication Data
US 2011/0032513 A1  Feb. 10, 2011

(30) Foreign Application Priority Data
Oct. 13, 2006 (FR) ...................... 06 08995

(51) Int. Cl.
*G01N 31/02* (2006.01)
*G01N 21/01* (2006.01)
*G01N 35/08* (2006.01)

(52) U.S. Cl.
USPC ................... 436/4; 422/81; 422/82; 422/402; 422/403; 422/412; 422/417; 422/502; 422/503; 422/537; 436/2; 436/52; 436/53; 436/179; 436/181

(58) Field of Classification Search .............. 422/81–82, 422/502–503, 402–403, 412, 417, 537; 436/2, 436/52–53, 163, 179, 4, 181
See application file for complete search history.

(56) References Cited

U.S. PATENT DOCUMENTS 3,449,938 A * 6/1969 Giddings ..................... 73/23.39
3,799,742 A * 3/1974 Coleman ...................... 422/417
(Continued)

FOREIGN PATENT DOCUMENTS
DE  199 07 448 A1  8/2000
EP  1 306 674 A1  5/2003
(Continued)

OTHER PUBLICATIONS

Tondre, C. et al, "On an Automated Device for the Determination of Isotropic Microemulsion Phases of Ternary Systems Including a Nonionic Surfactant" Journal of Dispersion Science and Technology 1986, 7, 581-597.*

(Continued)

*Primary Examiner* — Arlen Soderquist
(74) *Attorney, Agent, or Firm* — SNR Denton US LLP (57) ABSTRACT

Fluid flow devices include a small plate (2), at least one flow channel (20) formed into this small plate, at least one storage channel (22$_1$-22$_6$) extending from this connection channel, and a set of valves (V$_1$-V$_6$), each of which is suitable for allowing or stopping the flow of fluid in a corresponding storage channel.

28 Claims, 7 Drawing Sheets

U.S. PATENT DOCUMENTS

| | | | | |
|---|---|---|---|---|
| 4,231,990 A * | 11/1980 | Jottier | | 422/510 |
| 4,479,762 A * | 10/1984 | Bilstad et al. | | 417/395 |
| 4,601,881 A * | 7/1986 | Webster | | 422/67 |
| 5,077,017 A * | 12/1991 | Gorin et al. | | 422/514 |
| 5,213,967 A * | 5/1993 | Erdman et al. | | 435/31 |
| 5,863,502 A * | 1/1999 | Southgate et al. | | 422/417 |
| 5,869,004 A * | 2/1999 | Parce et al. | | 422/504 |
| 5,948,684 A * | 9/1999 | Weigl et al. | | 436/52 |
| 5,972,710 A | 10/1999 | Weigl et al. | | |
| 6,004,822 A * | 12/1999 | Li et al. | | 436/177 |
| 6,045,755 A * | 4/2000 | Lebl et al. | | 506/33 |
| 6,130,098 A * | 10/2000 | Handique et al. | | 436/180 |
| 6,174,365 B1 * | 1/2001 | Sanjoh | | 117/68 |
| 6,454,924 B2 * | 9/2002 | Jedrzejewski et al. | | 204/601 |
| 6,458,325 B1 * | 10/2002 | Roscher et al. | | 422/68.1 |
| 6,615,856 B2 * | 9/2003 | McNeely et al. | | 137/14 |
| 6,637,463 B1 * | 10/2003 | Lei et al. | | 137/803 |
| 6,919,046 B2 * | 7/2005 | O'Connor et al. | | 422/502 |
| 7,112,444 B2 * | 9/2006 | Beebe et al. | | 436/52 |
| 7,122,156 B2 * | 10/2006 | Bergh et al. | | 422/606 |
| 7,125,711 B2 * | 10/2006 | Pugia et al. | | 435/288.5 |
| 7,150,994 B2 * | 12/2006 | Bergh et al. | | 436/37 |
| 2002/0143437 A1 * | 10/2002 | Handique et al. | | 700/266 |
| 2002/0145231 A1 * | 10/2002 | Quake et al. | | 264/267 |
| 2002/0153046 A1 * | 10/2002 | Dantsker et al. | | 137/833 |
| 2003/0005967 A1 * | 1/2003 | Karp | | 137/806 |
| 2003/0082081 A1 | 5/2003 | Fouillet et al. | | |
| 2003/0166265 A1 * | 9/2003 | Pugia et al. | | 435/288.3 |
| 2003/0210607 A1 * | 11/2003 | Gilbert et al. | | 366/152.1 |
| 2004/0115731 A1 * | 6/2004 | Hansen et al. | | 435/7.1 |
| 2004/0115838 A1 | 6/2004 | Quake et al. | | |
| 2004/0209381 A1 * | 10/2004 | Peters et al. | | 436/177 |
| 2005/0019933 A1 * | 1/2005 | Andersson et al. | | 436/52 |
| 2005/0087122 A1 * | 4/2005 | Ismagliov et al. | | 117/2 |
| 2005/0229839 A1 | 10/2005 | Quake et al. | | |
| 2005/0255600 A1 * | 11/2005 | Padmanabhan et al. | | 436/63 |
| 2005/0266582 A1 * | 12/2005 | Modlin et al. | | 436/164 |
| 2006/0094119 A1 | 5/2006 | Ismagliov et al. | | |
| 2007/0028969 A1 * | 2/2007 | Boyd et al. | | 137/606 |
| 2009/0325276 A1 * | 12/2009 | Battrell et al. | | 435/287.2 |
| 2010/0129917 A1 * | 5/2010 | Panizza et al. | | 436/52 |

FOREIGN PATENT DOCUMENTS

| | | | |
|---|---|---|---|
| WO | 98/43049 | * | 10/1998 |
| WO | WO 03/037514 A | | 5/2003 |

OTHER PUBLICATIONS

Chao et al., "Control of Concentration and Volume Gradients in Microfluidic Droplet Arrays for Protein Crystallization Screening," Proceedings of the 26$^{th}$ Annual International Conference of the IEEE EMBS, Sep. 1-5, 2004, San Francisco, CA, USA, pp. 2623-2626.

* cited by examiner

FLUID FLOW DEVICE AND ASSEMBLY EMPLOYING A TEMPERATURE GADIENT FOR DETERMINING AT LEAST ONE CHARACTERISTIC OF A PHYSICO-CHEMICAL SYSTEM THEREWITH

CROSS-REFERENCE TO EARLIER APPLICATIONS

This application is the United States national phase of PCT/FR 2007/001667, filed Oct. 12, 2007 and designating the United States (published in the French language on Apr. 24, 2008, as WO 2008/046989 A1; the title and abstract were also published in English), which claims priority under 35 U.S.C.§119 of FR 0608995, filed Oct. 13, 2006, each hereby expressly incorporated by reference in its entirety and each assigned to the assignee hereof.

The present invention relates to a fluid flow device, an assembly for determining at least one characteristic of a physico-chemical system comprising such a device, a determination method employing this assembly, and a corresponding screening method.

In the sense of the invention a physico-chemical system, of which it is proposed to determine at least one characteristic, may be a pure substance, but also a compound, such as one or more solute(s) dissolved in a solvent for example, or alternatively a mixture of several pure substances. In the sense of the invention a characteristic of this physico-chemical system is in particular a characteristic curve of such a system, in particular a thermodynamic limit, especially a phase diagram, such as a solubility curve, or alternatively the miscibility limit for a mix of two liquids.

The present invention aims more specifically, but not exclusively, to study the solubility of such a physico-chemical system. Recall that the solubility of a solute in a solvent is the maximum concentration of this solute that can be dissolved in this solvent at a given temperature. The solubility curve of this solute, which therefore forms a physico-chemical system according to the invention, corresponds to the variation of this solubility as a function of temperature.

The methods conventionally used to determine this solubility curve are diverse. They make use of various measurements, in the course of which at least one parameter is modified, in particular the solute concentration and/or the temperature. Generally speaking, the methods employed in the prior art are systematic in nature, so that they prove to take a particularly long time to implement.

In these conditions, the invention proposes to remedy this shortcoming. It aims in particular to propose a solution enabling reliable determination of at least one characteristic of a physico-chemical system, accompanied by an appreciably reduced handling time in relation to the prior art.

To this end, its subject is a fluid flow device, comprising:
a plate (2);
at least one connecting channel (20) formed in this plate.
several storage channels (22$_1$-22$_6$ extending from this connecting channel;
several valves (V$_1$-V$_6$), each of which is suited to allow or to stop the flow of fluid into a corresponding storage channel; and
means (32$_1$, 32$_2$) adapted to apply a gradient of at least one condition along each storage channel (22$_1$-22$_6$).

Further advantageous features of this device are characterized in that this device furthermore comprises means (4, 6, 12, 18) for forming a succession of slugs (G$_1$-G$_6$) in a carrier phase (P) in the connecting channel (20) and each storage channel (22); particularly when the means for forming slugs comprise at least a first feed channel (4, 6) for the component(s) of said slugs, along with a second feed channel (12) for the carrier phase, forming an intersection with the or each first feed channel; and/or when the cross section of the connecting channel (20) and of each storage channel (22$_1$-22$_6$) is between 100 µ$^2$ and 25 mm$^2$, particularly when the connecting channel and each storage channel are microchannels (20, 22$_1$-22$_6$), the cross section of which is between 100 µm$^2$ and 1 mm$^2$ and/or wherein each valve (V$_1$-V$_6$) is of the tube-pinching type. The fluid flow device as defined above can be further characterized in that the opening (22'$_1$) of each storage channel (22$_1$-22$_6$) is connected with a corresponding valve (V$_1$-V$_6$) by means of a connecting member (24, 26) independent of the plate (2), can be further characterized in that the end of each storage channel (22$_1$-22$_6$) opposite the connecting channel (20) is connected with a rigid tube (24) which opens into a flexible tube (26) suited to cooperate with a corresponding tube-pinching valve (V$_1$-V$_6$); and/or can be further characterized in that the storage channels (22$_1$-22$_6$) are parallel to one another; particularly when the parallel storage channels (22$_1$-22$_6$) are perpendicular to the connecting channel (20). The fluid flow device as described above can be characterized in that between two and fifteen, preferably between five and ten, storage channels (22$_1$-22$_6$) are provided, particularly when the means adapted to apply a gradient comprise a first source (32$_1$) placed close to a first end of each storage channel, along with a second source (32$_2$) placed close to a second end of each storage channel, the first and second sources being adapted to apply different conditions, in particular different temperatures.

The subject of the invention is also an assembly for determining at least one characteristic of a physico-chemical system, comprising a fluid flow device as described above, analysis means (34) adapted to identify at least two different states of the physico-chemical system, or of a physico-chemical whole comprising said physico-chemical system, in each storage channel, along with processing means (36) connected to the analysis means (34).

The subject of the invention is also a method for determining at least one characteristic of a physico-chemical system employing a determination assembly as described in the preceding paragraph, in which method:
various fractions of said physico-chemical system (A) are infected into the various storage channels (22$_1$-22$_6$) while varying at least one parameter of this physico-chemical system (A) or of a physico-chemical whole (G$_1$-G$_6$) comprising this physico-chemical system, in the various channels, while keeping this parameter invariant in one and the same storage channel;
said fractions of the physico-chemical system are immobilized;
a gradient of at least one condition is applied along the various storage channels (22$_1$-22$_6$);
at least two different states are identified of the physico-chemical system, or of said physico-chemical whole (G$_1$-G$_6$), in the storage channels; and
from this, the or each characteristic of this physico-chemical system is deduced.

Further advantageous features of this method are the following:
The determination method as defined above, wherein the parameter which is varied is the composition of the physico-chemical system or of the physico-chemical whole comprising this system, particularly when the parameter which is varied is the concentration of the physico-chemical system in the physico-chemical whole; and/or the determination method as defined above, wherein the physico-chemical whole is formed by mixing the physico-chemical system, which is especially a solute, and an additive, especially a solvent, and the parameter which is varied is the nature of the additive, while preserving the same concentration of physico-chemical system in the physico-chemical whole;

Any determination method as defined above, wherein the parameter of the physico-chemical system or whole is varied proportionally, especially linearly, in relation to the distance separating the various storage channels ($22_r$-$22_6$);

Any determination method as defined above, wherein the condition on which a gradient is imposed is an operating condition, especially the temperature, relative humidity, or the illumination intensity;

Any determination method as defined above, wherein the two different states correspond to different phases of the physico-chemical system and/or whole; particularly when the different phases respectively correspond to the presence and to the absence, in the physico-chemical whole, of crystals formed by the physico-chemical system;

Any determination method as defined above, wherein the physico-chemical system and/or whole is in injected in the form of slugs, in particular drops ($G_1$-$G_6$) in a carrier phase (P) that is immiscible with these slugs;

Any determination method defined above, wherein the physico-chemical system is injected with a first value of the parameter in a first storage channel ($22_1$) while keeping a first valve ($V_1$) associated with this channel open and while keeping the other valves ($V_2$-$V_6$) closed, then said first valve is closed while opening a second valve ($V_2$) and the physico-chemical system is injected with a second value of the parameter in the second storage channel ($22_2$), then the physico-chemical system is injected in an iterative manner with other values of said parameter in the other storage channels;

Any determination method define above, wherein the various storage channels ($22_1$-$22_6$) are filled with a physico-chemical system and/or a physico-chemical whole in a first state, especially a liquid state, this system and/or whole is brought into a second state, especially a crystallized state, and said condition gradient is applied so as to bring only part of the system and/or of the whole back into the initial first state;

Any determination method as defined above, wherein said at least two different states are identified by analysis of the various fractions of the physico-chemical system injected into the storage channels; particularly when a visual analysis is carried out, especially using a microscope (34) associated with viewing apparatus, more especially when a spectroscopic analysis is carried out, in particular Raman or infrared spectroscopy;

Any determination method as described in the four preceding paragraphs, wherein for each storage channel ($22_1$-$22_6$) two adjacent values ($T'_i(1)$, $T''_i(1)$) of the parameter are identified which correspond to two different states of the slugs ($G_1$-$G_6$) and the mean of these two values is produced to obtain a characteristic value ($T_i$) of this parameter for each storage channel, especially when the characteristic curve of the physico-chemical system is a characteristic curve of this system and this characteristic curve is deduced from the various characteristic values ($T_1$-$T_6$).

The subject of the invention is finally a screening method for screening several physico-chemical systems, in which several physico-chemical systems are prepared, at least one characteristic of each physico-chemical system is determined as in one of the determination methods defined above, and at least one preferred physico-chemical system having at least one preferred characteristic is identified.

The invention will be described below with reference to the appended drawings, provided solely by way of nonlimiting example, in which.

Figure 1:
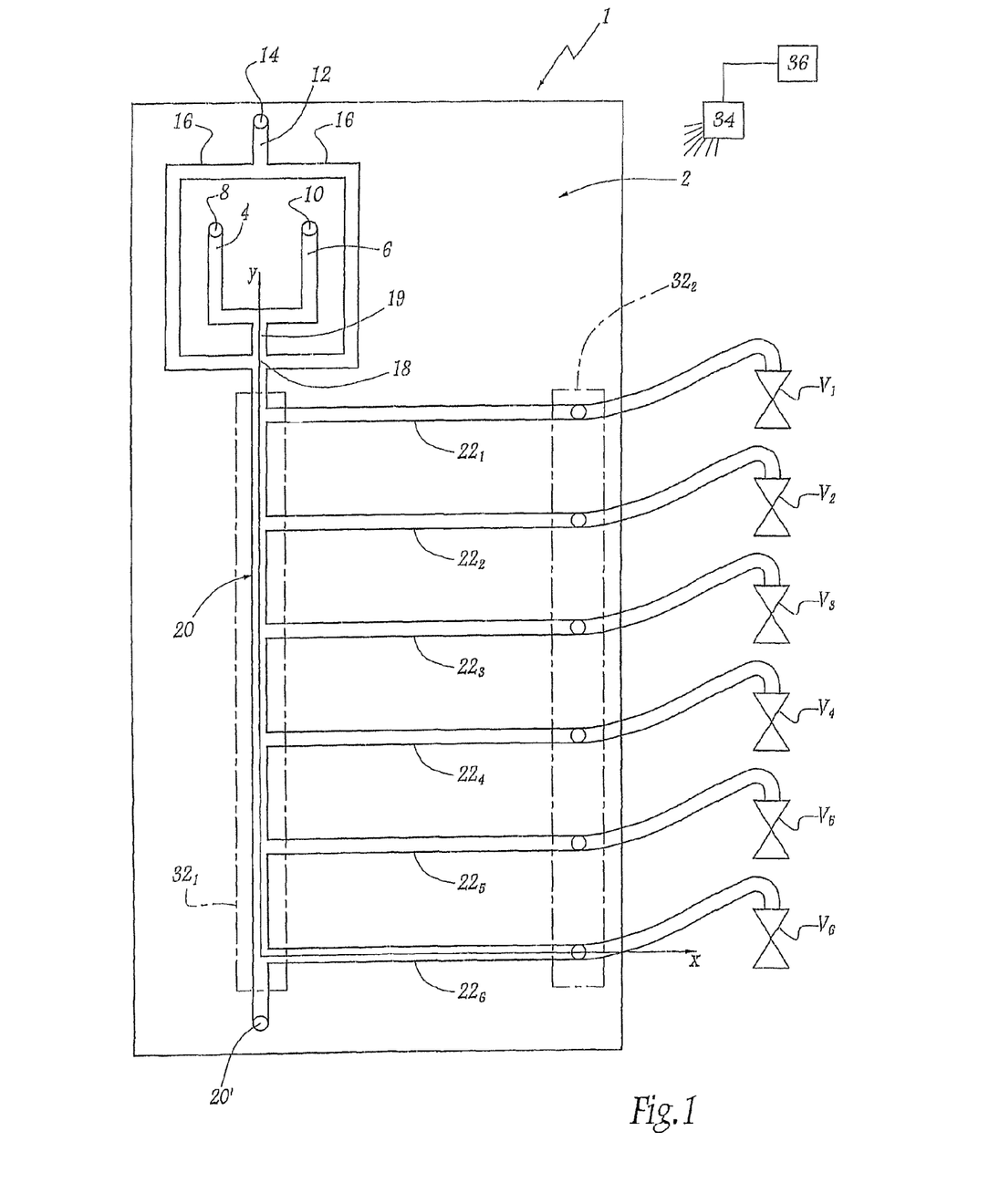
FIG. 1 is a front view schematically illustrating a determination assembly according to the invention.

FIG. 1 illustrates a determination assembly according to the invention which comprises first of all a fluid flow device, denoted as a whole by the reference number 1. This device comprises a plate 2 which is made in a manner known per se, for example made of PDMS (polydimethylsiloxane). However, by way of a variant, it is possible to envisage forming it of any other suitable material, such as glass, silicon, PMMA (poly(methyl methacrylate)), or alternatively a photosensitive resin of the type SU-8 by the company MicroChem, or of the type NOA by the company Nordland.

This plate 2 has a length and a width typically between 5 and 10 cm, and a typical thickness of 5 mm. It is etched with various microchannels according to conventional procedures of the prior art, which are described in particular in "D. C. DUFFY, J. C. McDONALD, Olivier J. A. SCHUELLER, George M. WHITESIDES, ANAL. CHEM., 70, pp. 49744984, 1998".

In the example illustrated, the characteristic cross sectional area of these microchannels is typically between 100 $\mu m^2$ (for example 10 $\mu m$ by 10 $\mu m$) and 1 $mm^2$ (for example 1 mm by 1 mm). This size typically causes a laminar flow within these microchannels, with a Reynolds number less than 10. By way of indication, to illustrate the properties of these microchannels, the work by Stéphane COLIN may be mentioned, Microfluidique (EGEM microsystems series, published by Hermes Sciences Publications).

It will, however, be noted that, by way of a variant, the invention can also be applied to millifluidic flow channels, that is channels whose cross section is greater than the values mentioned above. Thus, the cross section of these millifluidic channels may reach a value close to 9 $mm^2$, or 3 mm by 3 mm for example, or even close to 25 $mm^2$, or 5 mm by 5 mm for example.

FIG. 1 illustrates in particular detail the design of the microchannels that are engraved on the plate 2. Two feed microchannels 4 and 6 are found first of all, feeding two first components, which are associated with two inlets 8 and 10. Each of the latter is suited to receive a first end of a tube that is not shown, the other end of which is connected to a syringe, also not shown. In conventional manner, the flow rate of the component administered by each syringe is controlled by means of a syringe pump, also not shown.

In addition, a microchannel 12 is provided, associated with an inlet 14 which interacts with a tube, with a syringe, and with a syringe pump, which are not shown. This microchannel 12 is divided into two branches 16 making roughly the shape of a square, which meet again at an intersection 18. A mixing microchannel 19, into which the downstream ends of the two microchannels 4 and 6 open, interacts with this intersection 18.

Downstream of the intersection 18, that is to say below the latter in FIG. 1, a channel called the connecting channel 20 extends longitudinally, in this case vertically. This connecting channel 20 is provided with an outlet 20', which, it should be noted, is optional. It is caused to interact with several channels called storage channels $22_1$ to $22_6$. In the sense of the invention, the term "several" means "at least two".

In the example illustrated, these storage microchannels extend horizontally, that is to say that they are parallel to each other while being perpendicular to the connecting channel 20. However, it is possible to make provision for these storage channels not being perpendicular to the connecting channel and not being parallel to each other. Thus, it is possible to arrange them around a circle.

As FIG. 1 shows, the connecting channel 20 and the various storage channels $22_1$ to $22_6$ define a comb, the base of which is formed by the connecting channel and the teeth of which are formed by the storage channels. By analogy with electricity, the various storage channels thus extend in parallel from this connecting channel.

It is furthermore possible to note that this connecting channel and these storage channels define a quadrilateral, one side of which is formed by the connecting channel 20, two additional sides of which are defined by the end storage channels $22_1$ and $22_6$, and a last side of which is defined by a segment parallel to the connecting channel 20 which links the downstream outlets of the various storage channels. In the example illustrated the aforementioned quadrilateral is a rectangle.

In the example illustrated, the storage microchannels $22_1$ to $22_6$ are represented as six in number. However, in practice a number of these channels is used that is advantageously between two and fifteen, preferably between five and ten. It is also possible to envisage using a single storage microchannel.

Figure 2A:
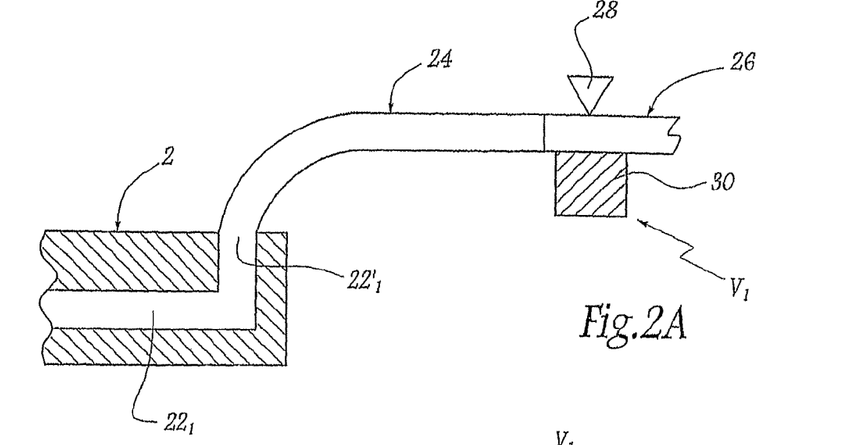
FIGS. 2A and 2B are side views illustrating two positions of a valve equipping the determination assembly of FIG. 1.
Figure 2B:
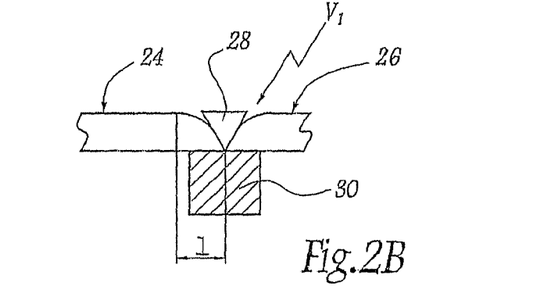

At their downstream end, situated on the right of FIG. 1, the storage microchannels interact with valves $V_1$ to $V_6$, illustrated schematically, one $V_1$ of which is shown in greater detail in FIGS. 2A and 2B. The opening $22'_1$ of the microchannel $22_1$ is connected with a rigid tube 24, made for example of fluorinated ethylene propylene (Teflon® FEP) or polyetheretherketone (PEEK®), that is to say that it does not radially deform appreciably when a liquid is flowing. This rigid tube 24 then opens into a flexible tube 26, made of PVC or silicone for example, which is associated with the valve $V_1$. The latter is a tubepinching solenoid valve, of a type known per se.

It should be highlighted that the tubes 24 and 26 form a connecting member, linking the opening $22'_1$ of the microchannel $22_1$ with the valve V. This connecting member is independent of the plate, that is to say it may be fitted, especially in a removable manner, to the walls of the aforementioned opening. This is advantageous to the extent that it is possible to make the plate 2 of any material, independently of the nature of the valve and its connecting member.

This solenoid valve $V_1$ is provided in a conventional manner with a piston 28 suited to being actuated by a coil (not shown), capable of squashing the tube 26 against a support 30. It should be noted that the length l of the flexible tube 26, between its connection with the rigid tube 24 and the area pinched by the piston 28, is very small, for example close to 2 mm. This makes it possible to limit parasitic movements of the fluid in the various channels when the valve is being operated.

The structure of the valve shown in FIGS. 2A and 2B is advantageous. This is because this valve is physically isolated, due to the presence of the flexible tube 26, in relation to the fluid present in the storage microchannels. Furthermore, this valve is reliable while having a cost price that is relatively low.

As will emerge more clearly from what follows, the invention foresees applying two gradients along the two dimensions x and y, respectively defined by the storage microchannels 22 and the connecting microchannel 20. In this case, in the xdirection, in particular an operating condition gradient is applied, especially of temperature, humidity, illumination, or alternatively of the concentration of another compound.

In these conditions, the determination assembly according to the invention comprises means making it possible to apply such a gradient along the channels 22. In the example illustrated these means comprise two Peltier effect modules $32_1$ and $32_2$ making it possible to apply a temperature gradient. In a manner known per se, a Peltier effect module is able to cause temperature variations as a function of an electric current that is applied to it. Without in any way being limiting, it is possible to use modules corresponding to those marketed by the company Melcor under the reference CPI 4-71-06L.

The first $32_1$ of these modules is located close to the upstream end of the storage microchannels 22, illustrated on the left of FIG. 1. Furthermore, the second $32_2$ of these modules is provided close to the downstream end of these same channels, namely that located on the right of this figure, where these two modules are shown in dot-and-dash lines. As will be seen in greater detail in what follows, each of these modules $32_1$ and $32_2$ is capable of constituting a hot source or a cold source, depending on the steps of the method according to the invention.

Finally, the determination assembly is provided with means suitable for analyzing the content of the various microchannels formed in the plate 2. In the example illustrated, visual analysis means are involved, namely a microscope 34 represented schematically, the beam of which is directed towards the various storage microchannels 22. The microscope 34, which is associated with viewing apparatus (not shown), is connected in a conventional manner to a processing computer 36.

The implementation of the determination assembly according to the invention, described above, will now be explained in what follows.

Figure 3:
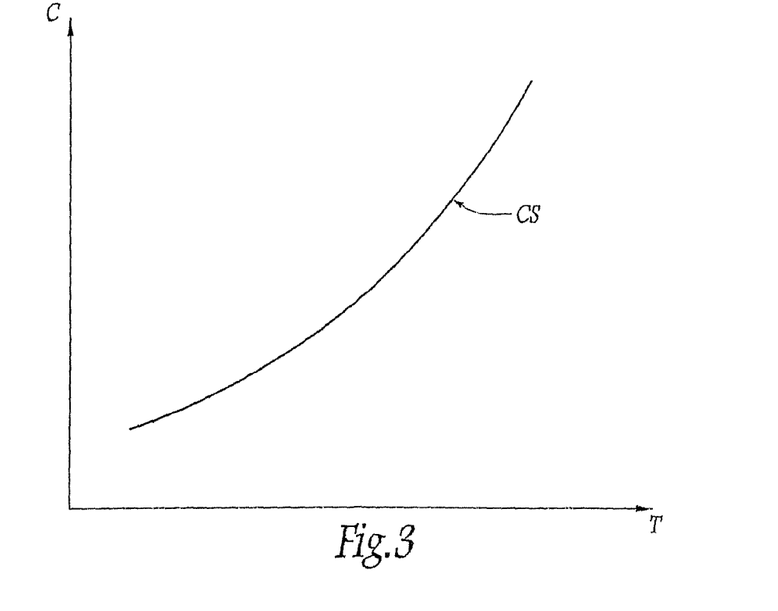
FIG. 3 is a graph illustrating a solubility curve that the invention proposes to determine.

In the example it is wished to determine the solubility curve of a solute in a solvent, such as that shown in FIG. 3. In the latter, the ycoordinates correspond to the solute concentration C in the solvent, while the temperature T is plotted on the xaxis. Thus, below and to the right of this solubility curve CS the solute is entirely liquid, while above and to the left of this same curve crystals of the solute may form in the solution.

In the sense of the invention, this solute A constitutes a physico-chemical system that the invention proposes to study, which may be introduced into the microchannel 4. Furthermore, the aforementioned solvent B may be admitted through the microchannel 6, so that the mixture of the solute and the solvent forms a physico-chemical whole in the sense of the invention. Finally, a carrier phase P, such as oil, which is immiscible with the mixture of the solute and the solvent, is admitted through the microchannel 12.

In a preliminary step, the various microchannels 20 and 22 are filled, along with the tubes 24 and 26, by means of oil or alternatively any suitable liquid, which makes it possible to eliminate problems due to the compressibility of air. The various valves $V_1$ to $V_6$ are moreover closed. Next, the first valve $V_1$ alone is opened (FIG. 4A), while admitting the solute A and the solvent B through the microchannels 4 and 6, and oil through the microchannel 12.

Figure 4A:
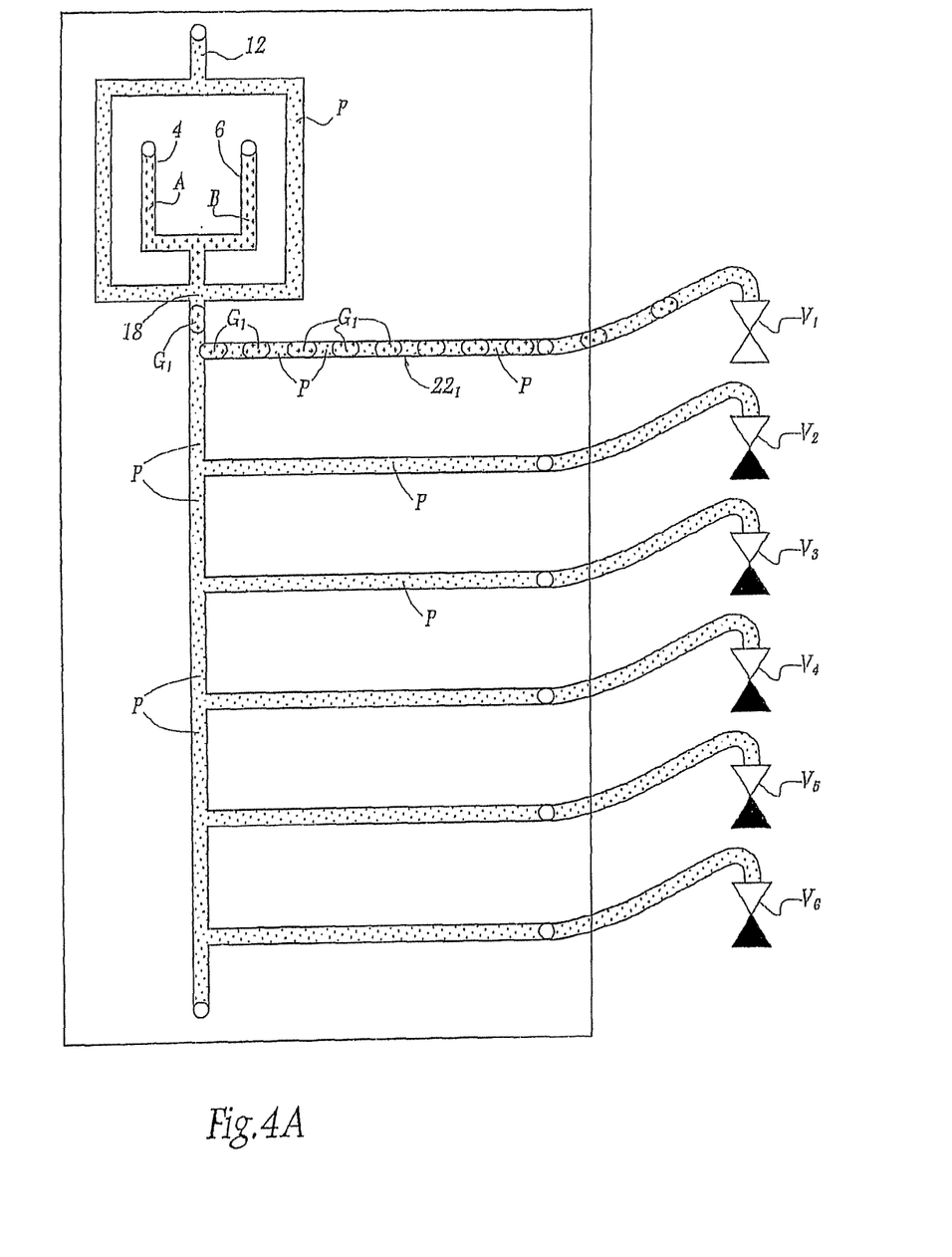
FIGS. 4A to 4C are front views, similar to FIG. 1, illustrating different steps of implementing the determination method according to the invention.

As this FIG. 4A shows, downstream of the intersection 18 a succession of drops $G_1$ is formed in a manner known per se, which drops are directed towards the first storage channel $22_1$. Each drop is formed by the mixture of the solute A and of the solvent B, that is to say the physico-chemical whole defined above. These drops $G_1$ are separated from each other in a conventional way by sections of oils, forming a carrier phase P that is immiscible with these drops. It will be noted that, during this step, a sufficiently high temperature is applied for the solute to be completely in liquid form within the drops $G_1$, that is to say below and to the right of the curve CS of FIG. 3.

The values of the respective flow rates of solute and solvent admitted by the channels 4 and 6 make it possible to know the concentration $C_1$ of solute in the various drops $G_1$. In this respect, the sum of flow rates of the solute and of the solvent is between 0.1 mL/hr and 5 mL/hr, especially between 0.5 and 1 mL/hr. The flow rate of oil, admitted through the microchannel 12, is between 0.5 and 10 mL/hr, especially between 1 and 5 mL/hr.

Once the first microchannel $22_1$ is filled with first drops $G_1$, the first valve $V_1$ is closed, according to the procedure made explicit in FIG. 2B, while opening the second valve $V_2$ (FIG. 4B), according to the procedure of FIG. 2A. Furthermore, the respective flow rates of solute and of solvent are modified so as to form drops $G_2$ in which the solute concentration $C_2$ is different to that $C_1$ previously mentioned.

Figure 4B:
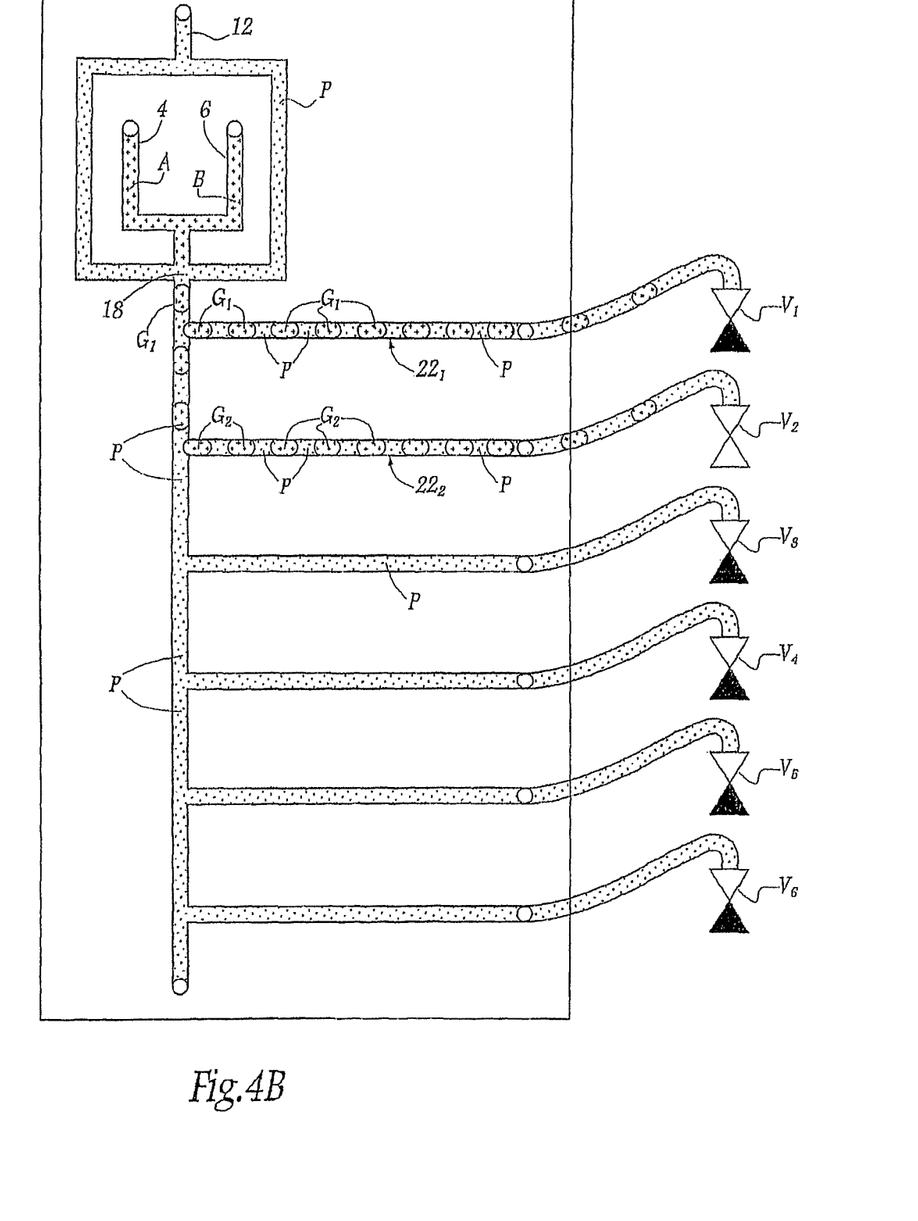

This then makes it possible to fill the second storage microchannel $22_2$ by means of a second type of drop $G_2$, as FIG. 4B illustrates. The various microchannels $22_1$ to $22_6$ are iteratively filled by means of different drops $G_1$ to $G_6$ for which the solute variations vary from $C_1$ to $C_6$.

It is advantageous that this concentration varies along the y-axis in the various microchannels 22. This concentration may thus vary in a determinable manner with the ycoordinates of the microchannels, especially in a monotonic manner, for example linearly, exponentially or alternatively logarithmically.

Figure 4C:
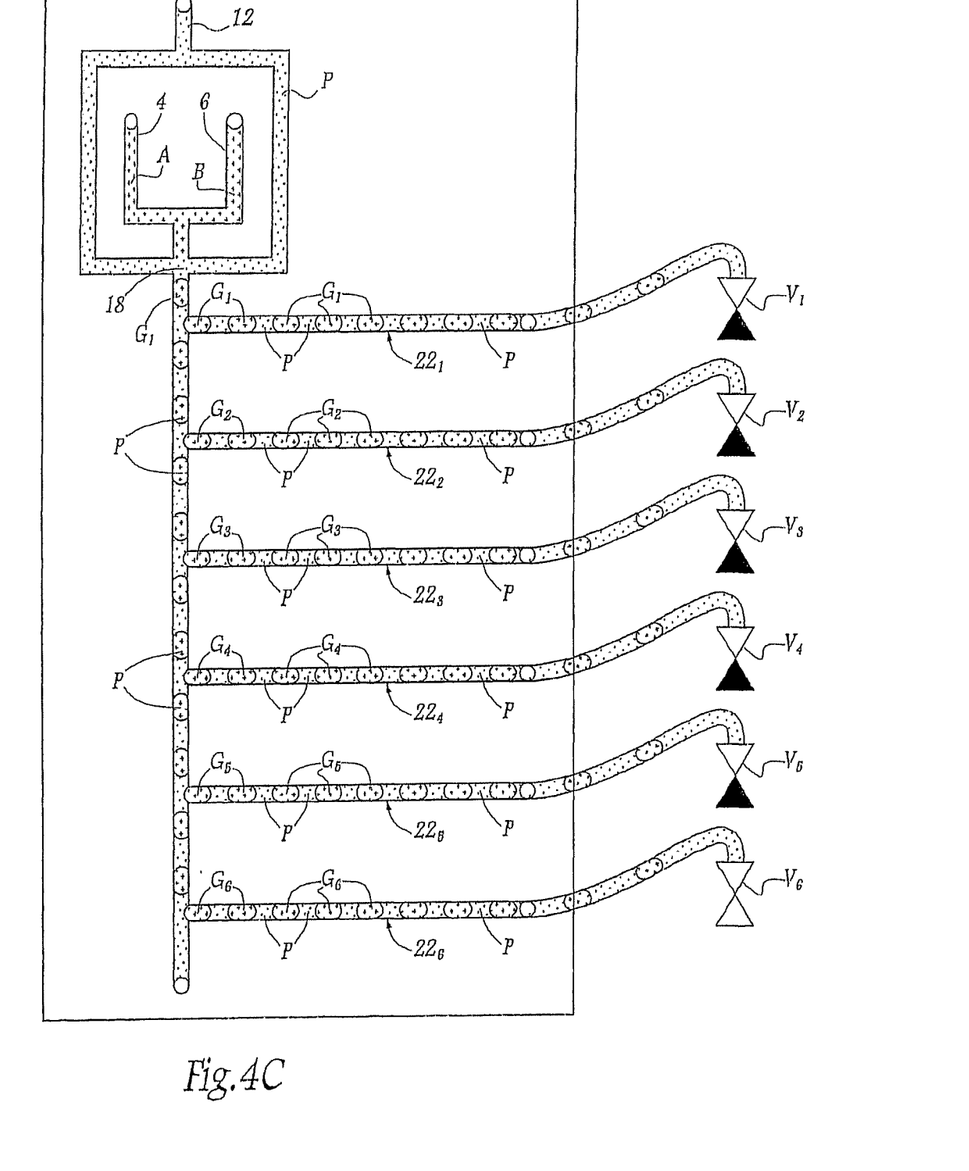

At the end of these various stages (see FIG. 4C) all the microchannels $22_i$, where i=1 to 6, have been filled by means of drops $G_i$. Moreover, for one and the same microchannel $22_i$ the concentration $C_i$ of solute in all the drops $G_i$ is identical while in the various channels $22_1$ to $22_6$ the concentrations $C_1$ to $C_6$ are different.

As previously mentioned, the filling of the various microchannels 22 has been carried out at high temperature so that the various drops $G_1$ to $G_6$ are in an entirely liquid state. The prevailing temperature in these microchannels 22 is then lowered so as to move towards the part situated above and to the left of the curve C of FIG. 3, and so as to crystallize the solute present in the whole of these drops. This temperature change is obtained by suitably changing the electric current supplied to the Peltier modules $32_1$ and $32_2$.

Next, a temperature gradient is applied along the various storage channels $22_1$ to $22_6$. To this end, the Peltier module on the left $32_1$ is controlled so as to generate a relatively low temperature at its surface, close for example to 10° C., while the module on the right $32_2$ is controlled so as to generate a relatively high temperature, for example of around 60° C. Given the nature of the plate 2, the application of these different temperatures leads to an approximately linear gradient along each microchannel 22. Thus, at the upstream end the temperature is close to that applied by the module $32_1$ while at the downstream end the temperature is close to that applied by the module $32_2$.

The fact that the various microchannels $22_1$ to $22_6$ are filled with different physico-chemical wholes makes it possible to vary the solute concentration along the yaxis. Moreover, the employment of Peltier modules $32_1$ and $32_2$ makes it possible to vary the temperature continuously along the x-axis. According to the invention, a frame of reference similar to that of the graph shown in FIG. 3 has therefore been recreated, as is illustrated in FIG. 5, where the concentration values $C_1$ to $C_6$ are borne on the y-axis.

An analysis step is then proceeded to so as to identify the drops of the storage microchannels 22 where crystals are present. This analysis is carried out visually by means of a microscope 34. Advantageously, this microscope 34 has a large field of vision so as to observe the whole of the plate at the same time. It is, for example, a binocular microscope.

By way of example, it is possible to carry out an observation via a crossed analyzer and polarizer in order to detect straightforwardly the presence of crystals that are birefringent. If the crystals are large enough, it is possible not to make use of birefringence.

Figure 5:
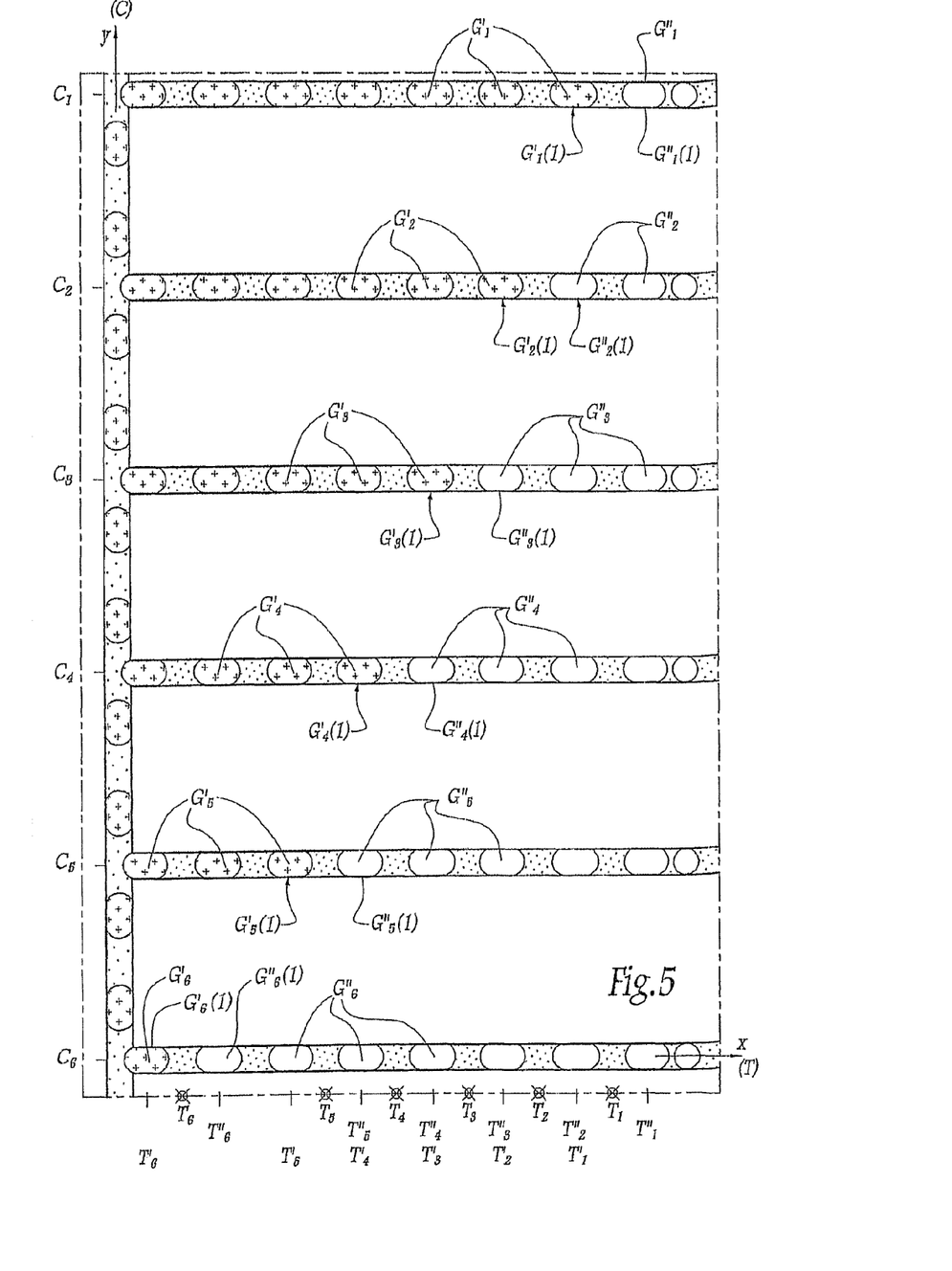
FIG. 5 is a larger scale view of FIG. 4.

For each storage microchannel, i.e. for i=1 to 6, in FIG. 5 $G_i'$ denotes the drops in which crystals are present and $G_i''$ the drops lacking them. For one and the same storage channel, the drops having crystals are situated on the left, that is to say on the side of the lowest temperature.

For each i from 1 to 6 $G_i'(1)$ and $G_i''(1)$ denote the two adjacent drops having different states, one of which is crystallized and the other not crystallized. In other words, the drop $G_i'(1)$ is the drop having the highest temperature among all those crystallized, while the drop $G_i''(1)$ is the drop having the lowest temperature among all those not crystallized. From this two temperatures, denoted $T_i'$ and $T_i''$ respectively, which correspond to the drops thus identified, are then deduced.

From this the solubility temperature $T_i$ is then deduced for each concentration $C_i$, where i=1 to 6:

$$Ti=(T_i'+T_i'')/2.$$

Figure 6:
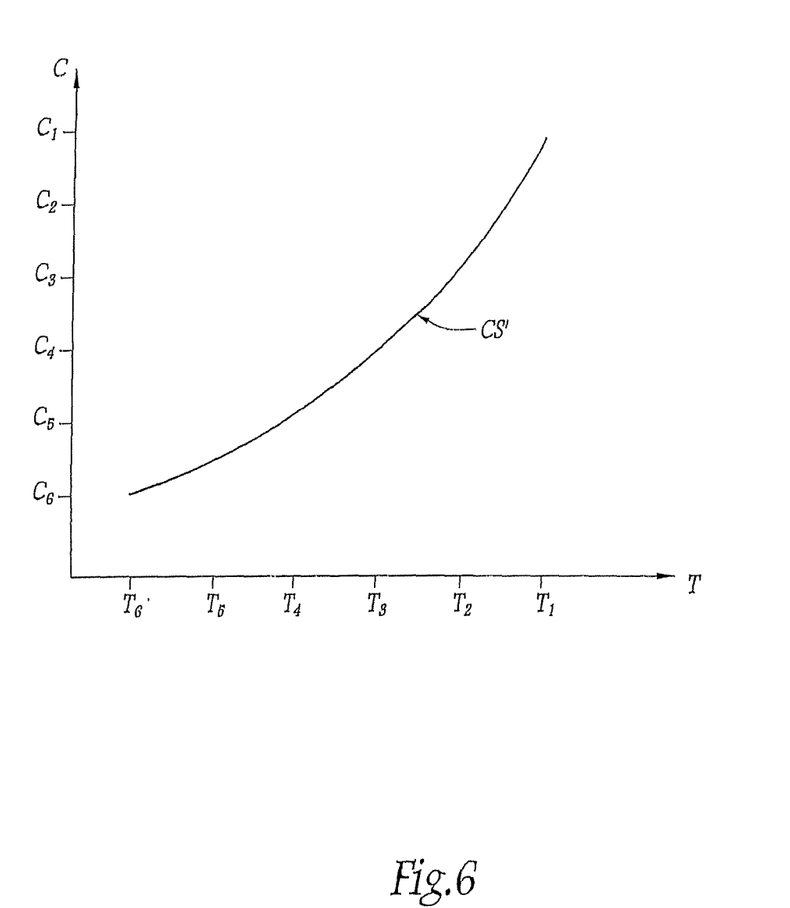
FIG. 6 is a graph, similar to FIG. 3, on which a curve obtained according to the invention is plotted.

The computer 36 then locates the various values $T_1$ to $T_6$ thus obtained for the concentrations $C_1$ to $C_6$ on the graph of FIG. 6. From these various points a solubility curve CS' is therefore obtained, shown in FIG. 6, which is close to that CS of FIG. 3.

In the example previously described, the solubility curve has been traced starting with six points, corresponding to six storage microchannels. It will be understood that if it is wished to improve the precision of the method of the invention, this involves increasing the number of storage microchannels, which makes it possible to increase correspondingly the number of points from which the solubility curve is produced. It is also possible to increase the number of drops present in one and the same storage channel, which contributes to reducing the distance between two adjacent drops. This makes it possible to improve the precision on the solubility temperature.

At the end of implementing the steps described above, it will have been possible to determine a characteristic of the physico-chemical system to be studied, namely its solubility curve. It is then possible to recommence this series of steps with another physico-chemical system while associating it with the same solvent and preserving the same concentrations and the same temperature gradient. These steps are carried out iteratively for an entire range of physico-chemical systems so that, at the end of the screening method thus implemented, it is then possible to identify at least one physico-chemical system that is advantageous depending on the intended application.

The invention is not limited to the example described and shown.

Thus, in this example the concentration of the solute varies along the yaxis, that is to say for the different channels. However, it is possible to vary another parameter of the physico-chemical system which the invention proposes to study.

Thus it is possible to admit, through the microchannel 4, a first liquid comprising a solute and a first type of solvent and, through the microchannel 6, a second liquid formed of the same solute and a second solvent that is miscible with the first solvent. By adjusting the flow rates injected into these microchannels, the storage channels are filled by means of a physico-chemical whole for which the solute concentration is constant but the proportion of the two aforementioned solvents is variable.

By way of an additional variant, it is also possible to vary, along the yaxis, the percentage of impurities present in the physico-chemical whole constituted by the solute and the solvent. In this case, a solution with a given solute concentration is injected into the channel 4. Moreover, this same solution is injected, into the channel 6, which solution additionally comprises a given concentration of impurities, such as nanoparticles or molecules. Thus, according to the ratio of the flow rates, the concentration of impurities in the drops tends to vary.

By way of additional example, it is possible to make provision for studying diagrams of liquidliquid equilibrium phases, for example ethanolhexadecane.

Along the yaxis the proportion of one liquid relative to the other is varied and a temperature gradient is applied along the xaxis. A limit is then observed between homogeneous drops and drops consisting of two immiscible liquids.

In the example taken up and shown, the temperature has been varied along the various storage channels, that is to say along the xaxis. However, it is possible to vary a different operating condition such as the relative humidity, the illumination or the variation in concentration of another compound.

In the example described and shown, the analysis is visual in type, due to the use of the microscope 34. However, by way of a variant, it is possible to provide for other types of analysis, especially Raman spectroscopy, infrared spectroscopy, UV or visible spectroscopy.

By way of an additional variant, it is possible to probe each drop by means of analysis apparatus, for example Raman spectroscope apparatus. This can be done automatically by locating the plate on a motorized and programmable table (x,y) of known type so as to locate each drop successively facing the analysis apparatus.

In the example described and shown, drops having two different states, namely a crystallized state and a noncrystallized state, are identified. However, these different states, identified according to the invention, may be of a different type, namely for example a simple liquid on the one hand, and the presence of two immiscible liquids on the other hand. It is thus possible to obtain a characteristic curve different from a solubility curve, namely the miscibility limit in the case of liquidliquid equilibria.

By way of an additional variant, it is also possible to produce a twodimensional map of a chemical reaction. Reactants are introduced at different concentrations into the storage microchannels, while the temperature or illumination along the xaxis is varied. The product of the corresponding reaction is then observed, for example by Raman spectroscopy.

In the example described and shown a succession of drops, forming slugs, are directed into the various storage microchannels. However, it is possible to inject directly a mixture of solute and solvent without using a carrier phase.

The invention makes it possible to attain the previously mentioned objectives.

Specifically, the operations of filling the various storage channels, carried out according to the invention, prove to be clearly faster than the successive operations that must be proceeded with in the prior art. Furthermore, it is possible, thanks to the invention, to carry out a direct reading of the characteristic sought, in particular by means of a simple visual analysis.

In addition, the possibility of forming, thanks to the invention, drops of particularly small volume is advantageous. This is because these drops are true microreactors which, given their scale, are homogeneous and therefore do not require agitation, as might be the case for macroscopic systems. This drop size also ensures rapid attainment of thermal equilibrium.

Moreover, the use of this microscopic scale makes it possible to limit the illtimed presence of impurities, which provides the determination thus carried out with great precision.

Finally, it should be noted that the use of slugs is advantageous in terms of the precision of the determination of the characteristic sought. Specifically, the various slugs present in the storage channels constitute individual entities, capable of thus preserving their original properties, in particular their initial concentration.

The invention claimed is:

1. A fluid flow device, comprising:
a plate;
at least one connecting channel formed in this plate;
a plurality of storage channels extending from this connecting channel, each of the storage channels having an upstream end, directed towards the connecting channel, and a downstream end directed away from the connecting channel;
at the downstream end of each storage channel, a valve for controlling the filling of the corresponding storage channel, each valve being adapted to allow or to stop the flow of fluid into the corresponding storage channel and these valves being adapted, by opening each valve while closing all of the other valves, to control the individual filling of the storage channels one after the other; and
both a first source, which is placed close to the upstream end of each storage channel and is adapted to apply a first temperature, and a second source, which is placed close to the downstream end of each storage channel and is adapted to apply a second temperature that is different from the first temperature so that the same substantially linear temperature gradient between the first and second temperatures is applied along all of the storage channels.

2. The fluid flow device as defined by claim 1, further comprising means for forming a succession of slugs in a carrier phase in the connecting channel and each storage channel.

3. The fluid flow device as defined by claim 2, said means for forming slugs comprising at least a first feed channel for the component(s) of said slugs, along with a second feed channel for the carrier phase, forming an intersection with the or each first feed channel.

4. The fluid flow device as defined by claim 1, wherein the cross-section of the connecting channel and of each storage channel ranges from 100 $\mu m^2$ to 25 $mm^2$.

5. The fluid flow device as defined by claim 4, wherein the connecting channel and each storage channel are microchannels, the cross-section of which ranges from 100 $\mu m^2$ to 1 $mm^2$.

6. The fluid flow device as defined by claim 1, wherein each valve is of tube-pinching configuration.

7. The fluid flow device as defined by claim 6, wherein the end of each storage channel opposite the connecting channel is connected with a rigid tube which opens into a flexible tube which cooperates with a corresponding tube-pinching valve.

8. The fluid flow device as defined by claim 1, wherein the opening of each storage channel is connected with the corresponding valve by means of a connecting member independent of the plate.

9. The fluid flow device as defined by claim 1, wherein the storage channels are parallel to one another.

10. The fluid flow device as defined by claim 9, wherein the parallel storage channels are perpendicular to the connecting channel.

11. The fluid flow device as defined by claim 1, comprising from two to fifteen storage channels.

12. An assembly for determining at least one characteristic of a physico-chemical system, comprising a fluid flow device as defined by claim 1, analysis means adapted to identify at least two different states of the physico-chemical system, or of a physico-chemical entity comprising said physico-chemical system, in each storage channel, and with processing means connected to the analysis means.

13. A method for determining at least one characteristic of a physico-chemical system, employing a determination assembly as defined by claim 12, in which method:
by controlling iteratively the opening of each valve while the other valves are closed, various fractions of said physico-chemical system are injected and immobilized into the various storage channels while varying at least one parameter of this physico-chemical system or of a physico-chemical entity comprising this physico-chemical system, in the various channels, while maintaining this parameter in one and the same storage channel;
by controlling the first temperature of the first source and the second temperature of the second source, the same substantially linear temperature gradient between the first and second temperatures is applied along all of the storage channels;
at least two different states are identified of the physico-chemical system, or of said physico-chemical entity, in the storage channels; and
from this, the or each characteristic of such physico-chemical system is deduced.

14. The determination method as defined by claim 13, wherein the parameter which is varied is the composition of the physico-chemical system or of the physico-chemical entity comprising this system.

15. The determination method as defined by claim 14, wherein the parameter which is varied is the concentration of the physico-chemical system in the physico-chemical entity.

16. The determination method as defined by claim 13, wherein the physico-chemical entity is formed by mixing the physico-chemical system, which is optionally a solute, and an additive, optionally a solvent, and the parameter which is varied is the nature of the additive, while preserving the same concentration of physico-chemical system in the physico-chemical entity.

17. The determination method as defined by claim 13, wherein the parameter of the physico-chemical system or entity is varied proportionally, optionally linearly, in relation to the distance separating the various storage channels.

18. The determination method as defined by claim 13, wherein the two different states correspond to different phases of the physico-chemical system and/or entity.

19. The determination method as defined by claim 18, wherein the different phases respectively correspond to the presence and to the absence, in the physico-chemical entity, of crystals formed by the physico-chemical system.

20. The determination method as defined by claim 13, wherein the physico-chemical system and/or entity is injected in the form of slugs, optionally drops, in a carrier phase that is immiscible with these slugs.

21. The determination method as defined by claim 20, wherein, for each storage channel, two adjacent values of the parameter are identified which correspond to two different states of the slugs and the mean of these two values is produced to obtain a characteristic value of this parameter for each storage channel.

22. The determination method as defined by claim 21, wherein the characteristic of the physico-chemical system is a characteristic curve thereof and this characteristic curve is deduced from the various characteristic values.

23. The determination method as defined by claim 13, wherein the physico-chemical system is injected with a first value of the parameter in a first storage channel while maintaining a first valve associated with this channel open and while maintaining the other valves closed, then said first valve is closed while opening a second valve and the physico-chemical system is injected with a second value of the parameter in the second storage channel, then the physico-chemical system is injected in an iterative manner with other values of said parameter in the other storage channels.

24. The determination method as defined by claim 13, wherein the various storage channels are filled with a physico-chemical system and/or a physico-chemical entity in a first state, optionally a liquid state, this system and/or entity is brought into a second state, optionally a crystallized state, and said condition gradient is applied to bring only part of the system and/or of the entity back into the initial first state.

25. The determination method as defined by claim 13, wherein at least two different states are identified by analysis of the various fractions of the physico-chemical system injected into the storage channels.

26. The determination method as defined by claim 25, wherein a visual analysis is carried out, optionally employing a microscope associated with viewing apparatus.

27. The determination method as defined by claim 25, wherein a spectroscopic analysis is carried out, optionally Raman or infrared spectroscopy.

28. A method of screening several physico-chemical systems, in which several physico-chemical systems are provided, at least one characteristic of each physico-chemical system is determined as defined by claim 13, and at least one preferred physico-chemical system having at least one preferred characteristic is identified.

* * * * *